(12) United States Patent
Perlman (10) Patent No.: US 10,532,076 B2
(45) Date of Patent: Jan. 14, 2020

(54) PROBIOTIC ANHYDROUS FATTY FOODSTUFFS AND METHODS OF MAKING SAME

(71) Applicant: Brandeis University, Waltham, MA (US)

(72) Inventor: Daniel Perlman, Arlington, MA (US)

(73) Assignee: Brandeis University, Waltham, MA (US)

( * ) Notice: Subject to any disclaimer, the term of this patent is extended or adjusted under 35 U.S.C. 154(b) by 0 days.

(21) Appl. No.: 15/941,339

(22) Filed: Mar. 30, 2018

(65) Prior Publication Data

US 2019/0015464 A1     Jan. 17, 2019

Related U.S. Application Data

(60) Provisional application No. 62/531,734, filed on Jul. 12, 2017.

(51) Int. Cl.
| | |
|---|---|
| *A61K 35/747* | (2015.01) |
| *A61K 9/00* | (2006.01) |
| *A23L 33/135* | (2016.01) |
| *A23L 25/10* | (2016.01) |
| *A23L 33/115* | (2016.01) |
| *A61K 9/14* | (2006.01) |
| *A61K 35/745* | (2015.01) |
| *A61K 35/742* | (2015.01) |

(52) U.S. Cl.
CPC ............ *A61K 35/747* (2013.01); *A23L 25/10* (2016.08); *A23L 33/115* (2016.08); *A23L 33/135* (2016.08); *A61K 9/0056* (2013.01); *A61K 9/14* (2013.01); *A23V 2002/00* (2013.01); *A23Y 2220/03* (2013.01); *A61K 35/742* (2013.01); *A61K 35/745* (2013.01)

(58) Field of Classification Search
CPC .... A23L 25/10; A61K 35/745; A23V 2002/00
See application file for complete search history.

(56) References Cited

U.S. PATENT DOCUMENTS

| | | | | |
|---|---|---|---|---|
| 6,010,737 A | * | 1/2000 | Meade | .................... A23L 25/10 426/607 |
| 9,107,429 B2 | | 8/2015 | Wassell | |
| 2002/0044990 A1 | * | 4/2002 | De Simone | .......... A23D 7/0056 426/61 |
| 2007/0160589 A1 | * | 7/2007 | Mattson | ............... A61K 35/745 424/93.45 |
| 2007/0207133 A1 | | 9/2007 | Wassell | |
| 2012/0058225 A1 | | 3/2012 | Kirejevas | |

FOREIGN PATENT DOCUMENTS

| | | |
|---|---|---|
| KR | 2011/0090217 A | 8/2011 |
| WO | 99/09839 A1 | 3/1999 |

OTHER PUBLICATIONS

Charteris et al., "Edible Table (Bio)Spread Containing Potentially Probiotic Lactobacillus and Bifidobacterium Species," Intl. J. Dairy Technol. 55(1):44-56 (2002).
Annie Harrison-Dunn, Spread the Word: Peanut Butter Delivers Probiotics Through Gastrointestinal Jeopardy, Nutra Ingredients (Jul. 21, 2015, 13:18 GMT), https://www.nutraingredients.com/Article/2015/07/21/Peanut-butter-delivers-probiotics-through-gastrointestinal-jeopardy#.
He et al., "Increased Water Activity Reduces the Thermal Resistance of Salmonella enterica in Peanut Butter," Appl. Environ. Microbiol. 79(15):4763-67 (2013).
Klu et al., "Survival of Four Commercial Probiotic Mixtures in Full Fat and Reduced Fat Peanut Butter," Food Microbiol. 44:34-40 (2014).
Klu et al., "Survival of Lactobacillus rhamnosus GG as Influenced by Storage Conditions and Product Matrixes," J. Food Sci. 77(12):M659-M663 (2012).
Soccol et al., "The Potential of Probiotics: A Review," Food Technol. Biotechnol. 48(4):413-34 (2010).
PCT/US2018/41794, International Search Report and Written Opinion (dated Oct. 3, 2018).

* cited by examiner

*Primary Examiner* — Robert J Yamasaki
*Assistant Examiner* — Stephen A Perkins
(74) *Attorney, Agent, or Firm* — Pepper Hamilton LLP (57) ABSTRACT

The present technology relates to foodstuffs that contain a substantially anhydrous fatty food that is solid at room temperature and comprises a substantially anhydrous probiotic bacterial preparation dispersed therein. Methods of making such substantially anhydrous fatty foods are also disclosed.

22 Claims, 1 Drawing Sheet

PROBIOTIC ANHYDROUS FATTY FOODSTUFFS AND METHODS OF MAKING SAME

This application claims the benefit of U.S. Provisional Patent Application Ser. No. 62/531,734, filed Jul. 12, 2017, which is hereby incorporated by reference in its entirety.

This technology relates to substantially anhydrous fatty foods that are solid at room temperature and comprise a substantially anhydrous probiotic bacterial preparation dispersed therein, and methods of making such foods.

BACKGROUND OF THE TECHNOLOGY

Probiotics have been defined as viable gastrointestinal bacteria that provide health benefits when consumed in adequate dietary amounts by a host, e.g., by a human or other mammal. Over a hundred years ago, Metchnikoff suggested that lactic acid bacteria and fermented yogurt could contribute to human longevity. With the ability to modify the bacterial flora found in the gastrointestinal tract, and to replace harmful microbes with benign and useful microbes, biologists have sought and found evidence of medical benefits provided by probiotic bacteria. Claimed benefits of probiotics include a decrease in potentially pathogenic gastro-intestinal bacteria, reduction in gastrointestinal bloating, strengthening of the immune system, improvement in bowel regularity, resistance to allergens, protection of cellular organelles and host DNA from oxidative damage, and restoring natural gut microbiota in subjects receiving antibiotic treatment. A widely cited review article by Soccol et al. ("The Potential of Probiotics: A Review," *Food Technol. Biotechnol.* 48(4):413-34 (2010)) is useful in describing a wide variety of probiotic microorganisms, their function and their uses.

Probiotic bacteria have been added to a variety of solid, semi-solid and liquid food and beverage products containing varying amounts of nutrients and water. Such nutrients and water may or may not support the growth of these bacteria. Traditionally, freeze-dried preparations or hydrous forms of probiotic bacterial strains have been mixed with either an aqueous component such as a yogurt mixture or a fatty component of a food before being diluted and dispersed into the entirety of the food product. For example, probiotic margarines and table spreads have been described in the literature in which the fat content of the final food product may vary between 60% and 95% by weight, while the water content in the form of a water-in-oil (w/o) emulsion may range between 5%-40% by weight. In some instances, microencapsulation has been used to segregate probiotic bacteria from the water component in such spreads.

A study of the research literature shows that when probiotic bacteria are dispersed during or following the manufacture of a food product such as a fatty table spread, within a few months of storage either under refrigeration or at room temperature, a substantial loss in bacterial cell viability is detected. That is, colony forming units (CFUs) are significantly diminished over a period of months as evidenced, for example, by 10-, 100-, or even 1000-fold reduction in viable bacterial cell titers. (E.g., Klu et al., "Survival of Four Commercial Probiotic Mixtures in Full Fat and Reduced Fat Peanut Butter," *Food Microbiol.* 44:34-40 (2014).) For example, an aqueous table spread containing probiotic bacteria has been described previously. However, the titers of viable bacteria were severely diminished both during manufacture and storage. (See Charteris et al., "Edible table (bio)spread containing potentially probiotic *Lactobacillus* and *Bifidobacterium* species," *Int'l J. Dairy Tech.* 55(1):44-56 (2002).)

The present technology is directed to overcoming these and other deficiencies in the art.

SUMMARY OF THE TECHNOLOGY

One aspect of the present technology relates to a foodstuff comprising a substantially anhydrous fatty food, wherein the substantially anhydrous fatty food is solid at room temperature and comprises a substantially anhydrous probiotic bacterial preparation dispersed therein.

A second aspect of the present technology relates to a method of making a substantially anhydrous fatty food (e.g., culinary nut/seed/bean butter) that is solid at room temperature and comprises a substantially anhydrous probiotic bacterial preparation dispersed in the fatty food, said method comprising: (i) providing a slurry comprising a liquid oil and a substantially anhydrous probiotic bacterial preparation dispersed in the slurry; (ii) providing a substantially anhydrous fatty food, wherein the substantially anhydrous fatty food is solid at room temperature and comprises a structuring fat; and (iii) blending the slurry into the substantially anhydrous fatty food at a blending temperature, wherein the blending temperature is within the viability temperature range of the probiotic bacterial preparation and the structuring fat is substantially melted during said blending.

Provided herein are fatty foods and methods of making them. The fatty foods contain probiotic bacterial preparations dispersed within them that have significantly improved survival rates. The probiotic bacteria can survive in a food product over a period of months or even a year or more, and in particular when the food product is stored at room temperature (e.g., survival following storage for several months or even a year or more at 20-25° C.).

BRIEF DESCRIPTION OF THE DRAWINGS

FIG. 1 shows the viability of La-14 (*Lactobacillus acidophilus*) in various foods after storage at 4° C. for one to nine weeks. The expected bacterial concentration for each sample (DuPont Nutrition and Health titer) was 10,000 CFU/uL, which was reached and sustained only in peanut butter. No bacterial colonies were detected in those fats for which data points are missing (Smart Balance and butter after time zero and soybean oil after 3 weeks).

FIG. 2 shows the viability of La-14 (*Lactobacillus acidophilus*) in various foods after storage at 20° C. for one to five weeks. The expected bacterial concentration for each sample (DuPont Nutrition and Health titer) was 10,000 CFU/uL, which was reached and sustained only in peanut butter. No bacterial colonies were detected in those fats for which data points are missing (Smart Balance and butter after time zero and soybean oil after 4 weeks).

DETAILED DESCRIPTION

This technology relates to substantially anhydrous fatty foods. The substantially anhydrous fatty foods are solid at room temperature and contain a substantially anhydrous probiotic bacterial preparation dispersed therein.

Substantially anhydrous fatty foods that are solid at room temperature are widely marketed and are shown herein to be potentially attractive and functionally effective vehicles for providing and stabilizing probiotic bacteria. It is believed that the predominant long term loss of probiotic bacterial viability in many processed foods that have been supplemented with probiotics can be attributed to the presence of moisture in the food, e.g., >1% by weight water, even if the food product is a fatty food such as butter or margarine. Furthermore, there are chemical variables that may reduce bacterial viability in any moisture-containing environment. These include pH changes, hydrolytic damage in an aqueous environment, exposure to molecular oxygen, free radical oxidation and unpredictable chemical reactions occurring in such an environment. For example, a water-in-oil emulsion or a moisture-containing food ingredient added to a fat-based processed food product may contribute significant "water activity." Water activity ($a_w$) is defined as the ratio of the water vapor pressure generated by the food product compared to the vapor pressure of pure water at the same temperature, e.g., often room temperature. Undesirable metabolic activity may be initiated in previously dormant probiotic bacterial cells exposed to any environment (including a fat environment) if water activity is sufficiently high. For example, with water activities of approximately 0.8 or greater, many mold and some bacteria may commence growth. Such higher water activities are undesirable because, once the probiotic cells experience moisture, lose their dormant condition, and begin growing, if the surrounding medium is incapable of providing adequate nutrients for bacterial growth, a loss of probiotic viability generally follows.

To mitigate many of the above problems, in the technology described herein a substantially anhydrous food environment is provided and its water activity is carefully monitored, for dispersing, stabilizing, and delivering probiotic bacteria to the health-conscious consumer. Substantially anhydrous fatty foods are good candidate vehicles for delivering probiotic bacteria. As disclosed herein, such fatty food vehicles that are solid or made solid at room temperature are unexpectedly effective in helping maintain probiotic viability. By way of example, the water activity in a culinary nut/seed/bean butter such as a typical peanut butter made from roasted peanuts (containing, for example, approximately 0.5% by weight moisture) is only approximately 0.25-0.40. Such low water activity numbers are compatible with maintaining bacterial dormancy for a wide variety of both vegetative and sporulated probiotic bacterial species. (See He et al., *Applied Environ'l Microbiol.* 79(15):4763-67 (2013), which is hereby incorporated by reference in its entirety).

A "substantially anhydrous" fatty food as used herein refers to a fat or oil with a water activity ($a_w$) at room temperature that is less than about 0.8, preferably less than 0.7. In at least one embodiment, the $a_w$ at room temperature is in a range having a lower limit of about 0.2, about 0.25, about 0.3, about 0.35, about 0.4, about 0.45, about 0.5, about 0.55, about 0.6, about 0.65, about 0.7, or about 0.75, and an upper limit of about 0.25, about 0.3, about 0.35, about 0.4, about 0.45, about 0.5, about 0.55, about 0.6, about 0.65, about 0.7, about 0.75, or about 0.8, in any combination thereof. In at least one embodiment, the range is about 0.2 to about 0.8, about 0.25 to about 0.4, about 0.3 to about 0.7, or about 0.3 to about 0.8. In at least one embodiment, the $a_w$ at room temperature is about 0.2, about 0.25, about 0.3, about 0.35, about 0.4, about 0.45, about 0.5, about 0.55, about 0.6, about 0.65, about 0.7, about 0.75, or about 0.8.

The term "fatty food" as used herein, refers to either a processed food product, or one or more animal or vegetable-derived edible fats or oils, or any combination thereof, containing edible fat-type molecules. In at least one embodiment, the fatty food contains approximately 25% to 99.9% by weight of fat-type molecules (e.g., monoglycerides, diglycerides, triglycerides, or combinations thereof). Typically, the fat-type molecules are primarily triglycerides. Mono- and diglycerides may be added to a triglyceride-based fat or oil for their emulsifying properties, for hardening, and/or to increase the melting temperature of the fat or oil.

The substantially anhydrous fatty foods of the present technology are solid at room temperature. As the most general definition as used herein, a "solid" fatty food is a food that maintains a solid crystalline matrix at room temperature such that it is sufficiently rigid enough to resist any obvious change in shape or spontaneous flow under its own weight. This includes plastic or soft solids that can be deformed into a new shape with external pressure (distinguished from elastic solids such as rubbers that return to an initial shape after pressure is released). For example, a solid fatty food would include a "natural style," i.e., fluid, culinary nut (e.g., peanut) butter that has been rendered solid at room temperature by addition and in situ crystallization of a structuring fat; if a jar containing such a nut butter is turned sideways or inverted, the nut butter remains inside the jar rather than flowing out.

One method suitable for identifying a solid fatty food according to the present technology would be the use of a penetrometer. A penetrometer generally measures the resistance of a substance to penetration to a given depth by a rigid weighted object such as a metal cone having a specified weight and specified conical taper angle dropped from a specified height. As an example of such a method, a steel cone having a 60 degree conical angle and weighing 79 g is first supported at the surface of the fatty food at room temperature (20-25° C.) and then released (zero drop height). In the present technology, a fatty food would be deemed to be solid at room temperature if the penetration by the penetrometer cone under these conditions is less than 25 mm (one inch). In at least one preferred embodiment (particularly for commercially marketable "soft solid" foods), penetration is at least 8 mm. For solid butters or spreads such as culinary nut/seed/bean butters and anhydrous butterfat (ghee) to be soft enough for spreadability (e.g., by knife or spatula), a modest penetration depth such as 5-20 mm (e.g., 14-18 mm) is preferred. As will be apparent to the skilled artisan, other methods that would provide analogous results could also be used to identify a solid fatty food according to the present technology.

The terms "substantially crystallized" and "substantially melted" as used herein refer to the physical state of a specific fat component, e.g., a structuring fat, present in a fatty food composition in which more than 50% by weight of that fat component exists in a either a crystalline state or alternatively in a melted state.

In at least one embodiment, the fatty food has an elevated viscosity (greater than 50,000 centipoise at room temperature).

Fatty foods that are solid at room temperature (or that can be made solid by addition of structuring fat) and are suitable for use in the present technology include substantially anhydrous culinary nut/seed/bean butters (made from ground nuts, tree nuts, seeds, or beans), anhydrous animal fats (e.g., anhydrous butterfat, such as ghee), and anhydrous vegetable fats and oils (e.g., palm fat, palm oil, palm olein, palm kernel oil, coconut fat, coconut oil, salad oils, canola oil, soybean oil, peanut oil, almond oil, hazelnut oil, cashew oil, pecan oil, pistachio oil, walnut oil, macadamia oil, Brazil nut oil, pumpkin seed oil, sesame seed oil, soybean oil, chia seed oil, sunflower oil, safflower oil, corn oil, cottonseed oil)

that can be further solidified, if necessary, by addition of structuring fat. As will be apparent to the skilled artisan, the substantially anhydrous fatty food according to the present technology can consist of a single type of fatty food or a mixture of two or more different types.

Suitable culinary nut butters according to the present technology include those of ground nuts and tree nuts, for example peanut butter (full fat or reduced fat), almond butter, hazelnut butter, cashew butter, pecan butter, pistachio butter, walnut butter, macadamia butter, Brazil nut butter, and blends of two or more different nuts. The nut butter can be crunchy or smooth. In at least one preferred embodiment, the fatty food is peanut butter. Culinary butters also include those made from seeds and beans, such as pumpkin seed, sesame seed, soybean, sunflower seed, safflower seed, and chia seed. Blends of two or more of these nuts, seeds, and/or beans are also contemplated.

The term "reduced fat" as used herein refers to a processed food product as described under the U.S. Code of Federal Regulations 21 C.F.R. § 101.62(b) (2016) (which is hereby incorporated by reference in its entirety), in which the food product contains at least 25 percent less fat per reference amount of food customarily consumed (e.g., per serving).

As described herein, with an unstabilized "natural style" culinary nut/seed/bean butter (containing liquid oil such as peanut oil; density 0.91), an added anhydrous probiotic material will rapidly sink through the nut/seed/bean butter due to the much greater density of the probiotic material. Thus, in at least one preferred embodiment, the culinary nut/seed/bean butter is made solid, i.e., "stabilized", with a "structuring fat" such as fully hydrogenated vegetable oil (e.g., hydrogenated soybean oil, canola oil, cottonseed oil, and combinations thereof) or a natural predominantly saturated fat such as palm stearin isolated from the palm fruit.

Suitable anhydrous semi-liquid or liquid oils can also be converted to fats that are solid at room temperature according to the present technology by adding an adequate amount of structuring fat. Anhydrous semi-liquid or liquid oils include salad oils (e.g., plain and herbal olive oils), palm oil, palm olein, palm kernel oil, coconut oil, canola oil, soybean oil, peanut oil, almond oil, hazelnut oil, cashew oil, pecan oil, pistachio oil, walnut oil, macadamia oil, Brazil nut oil, pumpkin seed oil, sesame seed oil, soybean oil, chia seed oil, sunflower oil, safflower, corn oil, cottonseed oil, other culinary nut oils, and mixtures thereof.

The fatty foods of the present technology contain a substantially anhydrous probiotic bacterial preparation dispersed in the fatty food.

A "substantially anhydrous" probiotic bacterial preparation as used herein refers to a probiotic bacterial preparation of one or more probiotic bacteria species, the preparation having a water activity ($a_w$) at room temperature that is less than about 0.8, preferably less than 0.7. In at least one embodiment, the $a_w$ at room temperature is in a range having a lower limit of about 0.2, about 0.25, about 0.3, about 0.35, about 0.4, about 0.45, about 0.5, about 0.55, about 0.6, about 0.65, about 0.7, or about 0.75, and an upper limit of about 0.25, about 0.3, about 0.35, about 0.4, about 0.45, about 0.5, about 0.55, about 0.6, about 0.65, about 0.7, about 0.75, or about 0.8, in any combination thereof. In at least one embodiment, the range is about 0.2 to about 0.8, about 0.25 to about 0.4, about 0.3 to about 0.7, or about 0.3 to about 0.8. In at least one embodiment, the $a_w$ at room temperature is about 0.2, about 0.25, about 0.3, about 0.35, about 0.4, about 0.45, about 0.5, about 0.55, about 0.6, about 0.65, about 0.7, about 0.75, or about 0.8. These values also correspond to the water activity measured for the probiotic component(s) and for any oil slurry containing the probiotic component(s).

Typical daily doses of probiotics may range from approximately $0.25 \times 10^9$ to approximately $10^{10}$ colony forming units (CFU) per serving of a supplemented food or beverage. Pure strains of vegetative bacteria can be purchased for food and dietary supplement use from a number of companies such as DuPont Nutrition and Health Inc. These probiotic strains are in the form of fine powders and are typically milled and sieved to produce particle sizes of approximately 100 mesh (150 microns) or smaller. Powder samples of the above bacterial strains having titers of approximately $3 \times 10^{11}$ CFU per gram powder have been obtained and used to achieve probiotic supplementation at levels of approximately $10^9$ CFU per serving of food. This level of supplementation typically requires using as little as 3 mg of bacterial powder per 15 g-30 g serving of fat or fatty food product. At a cost of $400 per kg, a 3 mg quantity ($10^9$ CFU) costs less than 0.15 cents per serving of food. For a 1 pound jar of peanut butter containing 14 servings, this supplementation level translates to approximately 2 cents per jar.

Vegetative probiotic bacterial species are easier to produce and less expensive than non-vegetative species such as sporulated bacterial species, and there is a much greater diversity of vegetative species. Thus, in at least one preferred embodiment, the probiotic bacterial preparation contains one or more vegetative bacterial species. Probiotic bacterial strains that have been cultured as vegetative bacterial cells can be subsequently freeze-dried to produce powders under conditions rendering the bacteria substantially anhydrous and dormant.

Although vegetative species are preferred, sporulated species such as *Bacillus coagulans* spores may also be used in the probiotic bacterial preparations of the present technology.

An exemplary non-exhaustive list of commercially available strains of probiotic bacteria suitable for use in the present technology include, without limitation, *Bacillus* (*Bacillus coagulans*), *Bifidobacterium* (*Bifidobacterium adolescentis, Bifidobacterium animalis, Bifidobacterium bifidum, Bifidobacterium breve, Bifidobacterium essencis, Bifidobacterium faecium, Bifidobacterium infantis, Bifidobacterium lactis, Bifidobacterium longum, Bifidobacterium longum* subsp. *infantis, Bifidobacterium pseudolungum*), *Lactobacillus* (*Lactobacillus acidophilus, Lactobacillus boulardii, Lactobacillus breve, Lactobacillus bulgaricus, Lactobacillus casei, Lactobacillus delbrueckii* ssp. *Bulgaricus, Lactobacillusfermentum, Lactobacillus gasseri, Lactobacillus helveticus, Lactobacillus paracasei, Lactobacillus plantarum, Lactobacillus reuteri, Lactobacillus rhamnosus, Lactobacillus rhamnosus* GG, *Lactobacillus salivarius*), *Lactococcus* (*Lactococcus lactis*), *Streptococcus* (*Streptococcus thermophilus*), *Pediococcus* (*Pediococcus acidilactici*), *Enterococcus* (*Enterococcus faecium*), *Leuconostoc, Carnobacterium, Proprioni bacterium*, and those described in Soccol et al., "The Potential of Probiotics: A Review," *Food Technol. Biotechnol.* 48(4):435-34 (2010), which is hereby incorporated by reference in its entirety. Much remains to be learned about the benefits of different probiotic species and many different species and varieties of Bifidobacteria and Lactobacilli as well as Bacilli are currently being selected for addition to a variety of processed foods. The fatty food can contain a single bacterial species, or blends containing two or more different species may be used.

Commercially available vegetative probiotic bacterial preparations include Danisco's FloraFIT® probiotics (Bb-02™ (*Bifidobacterium bifidum/Bifidobacterium lactis*), Bb-06™ (*Bifidobacterium bifidum*), Bb-03™ (*Bifidobacterium breve*), Bl -04™ (*Bifidobacterium lactis*), Bl-05™ (*Bifidobacterium longum*), Bi-07™ (*Bifidobacterium lactis*), Bi-26™ (*Bifidobacterium longum* subsp. *infantis*), La-14™ (*Lactobacillus acidophilus*), Lbr-35™ (*Lactobacillus breve*), Lb-64™ (*Lactobacillus bulgaricus*), Lc-11™ (*Lactobacillus casei*), Lg-36™ (*Lactobacillus gasseri*), Lpc-37™ (*Lactobacillus paracasei*), Lp-115™ (*Lactobacillus plantarum*), Lr-32™ (*Lactobacillus rhamnosus*), Ls-33™ (*Lactobacillus salivarius*), Ll-23™ (*Lactococcus lactis*), and St-21™ (*Streptococcus thermophilus*)). Commercially available sporulated probiotic bacterial preparations include Nebraska Culture's ProDURA® probiotic (*Bacillus coagulans*). Other commercially available probiotic bacterial preparations include Danisco's Howaru® probiotics (HOWARU®Bifido, HOWARU®Dophilus, HOWARU®Rhamnosus, HOWARU®Restore, and HOWARU®Balance). Equivalents of these commercial products are also contemplated.

In a preferred embodiment, the probiotic bacterial preparation is microencapsulated (e.g., as described in Soccol et al., "The Potential of Probiotics: A Review," *Food Technol. Biotechnol.* 48(4):435-34 (2010), which is hereby incorporated by reference in its entirety). Microencapsulated probiotic bacterial preparations are cohered dried masses of bacteria (aka conglomerated bacteria) in the form of particles, preferably having an average diameter in a range having a lower limit of about 10 microns, about 25 microns, about 50 microns, about 100 microns, or about 150 microns, and an upper limit of about 100 microns, about 150 microns, about 200 microns, or about 250 microns, in any combination thereof. In at least one embodiment, the range is about 10 to 250 microns, about 25 to about 200 microns, or about 100 to about 200 microns. In at least one preferred embodiment, the range is about 25 to about 150 microns, more preferably about 50 to about 100 microns. In at least one embodiment, the average diameter is about 150 microns.

In at least one embodiment, the probiotic bacterial preparation is present in a concentration of about 500 million CFU/serving. An average serving for peanut butter is about 30 grams.

As described herein, dispersing the substantially anhydrous probiotic bacterial preparation in a substantially anhydrous fatty food improves the long-term viability of the probiotic. In at least one embodiment of the present technology, the probiotic bacterial preparation has a 4-month survival rate at room temperature of greater than 10%, at least 25%, at least 50%, at least 75%, at least 90%, or at least 95%. In at least one embodiment, the probiotic bacterial preparation has a 12-month survival rate at room temperature of greater than 10%, at least 15%, at least 25%, at least 50%, at least 75%, at least 90%, or at least 95%. As used herein, a 4-month and 12-month survival rate refer to the percentage of viable cells that would survive if the fatty food were to be kept at room temperature for the indicated period. In at least one embodiment, the probiotic bacterial preparation is present in a concentration of at least 5 million CFU/g, at least 10 million CFU/g, at least 20 million CFU/g, or at least 50 million CFU/g after storage at room temperature for 12 months.

Typical methods of manufacturing peanut butter and nut butters in general are described in U.S. Pat. Nos. 5,202,147 and 6,312,754 and "How Products Are Made: Peanut Butter," http://www.madehow.com/Volume-1/Peanut-Butter.html (last accessed Mar. 9, 2017), each of which is hereby incorporated by reference in its entirety. These methods can be adapted, as described herein, to produce substantially anhydrous culinary nut/seed/bean butters having a substantially anhydrous probiotic bacterial preparation dispersed therein.

The substantially anhydrous fatty foods of the present technology can optionally contain other substantially anhydrous ingredients, such as sweeteners, salt, natural or artificial flavorings, fully dried fruit, nut and/or vegetable particles, coffee bean flour, biologically beneficial antioxidants, pharmacological agents such as vitamins, minerals and medicinal agents including but not limited to dried *cannabis* particles, other appetite stimulants, and analgesics, etc.

As will be apparent to the skilled artisan, the substantially anhydrous fatty foods of the present technology can be used or sold as-is or can be incorporated into another food. Thus, the present technology also includes foodstuffs that contain one or more substantially anhydrous fatty foods of the present technology. By way of example, a substantially anhydrous fatty food (e.g., culinary nut/seed/bean butter) of the present technology could be used to coat or fill a sweet or savory food, such as a candy (e.g., peanut butter cup), cereal, cracker, or the like. A substantially anhydrous fatty food (e.g., culinary nut/seed/bean butter) could also be mixed with another substantially anhydrous food, such as chocolate (e.g., a Nutella®-style spread). Typically, the overall composition of the foodstuff is also substantially anhydrous. However, foodstuffs that have a hydrous component could also be used, as long as there is a sufficient moisture barrier between the hydrous component and the substantially anhydrous fatty food of the present technology such that the substantially anhydrous fatty food of the present technology remains substantially anhydrous. For example, the substantially anhydrous fatty food could be coated (e.g., with a chocolate or candy coating) and then added to a hydrous foodstuff (e.g., chocolate- or candy-coated peanut butter in ice cream).

Another aspect of the present technology relates to a method of making a substantially anhydrous fatty food (e.g., culinary nut/seed/bean butter) that is solid at room temperature and comprises a substantially anhydrous probiotic bacterial preparation dispersed in the fatty food. This method involves (i) providing a slurry comprising a liquid oil and a substantially anhydrous probiotic bacterial preparation dispersed in the slurry; (ii) providing a substantially anhydrous fatty food, wherein the substantially anhydrous fatty food is solid at room temperature and comprises a structuring fat and; and iii) blending the slurry into the substantially anhydrous fatty food at a blending temperature, wherein the blending temperature is within the viability temperature range of the probiotic bacterial preparation and the structuring fat is substantially melted during said blending.

This method, in which a concentrated slurry of particulate probiotic material in a liquid oil is prepared before blending into any one of a variety of anhydrous fatty foods, helps assure that uniform and homogeneous distribution of the probiotic particles in a food will be achieved and then maintained at room temperature following solidification of the anhydrous fatty food upon crystallization of the structuring fat. Thus, blending is carried out before the melted structuring fat has substantially crystallized.

The manufacturing of culinary nut/seed/bean butters involves a grinding step, during which the nut/seed/bean butter reaches an elevated temperature (e.g., about 160-185° F.). The structuring fat is typically added at this stage. The nut/seed/bean butter is then cooled. In at least one embodiment of the present technology, the nut/seed/bean butter containing structuring fat is cooled to a blending temperature and the probiotic bacterial preparation (having been preferably pre-dispersed in an amount of liquid oil representing typically about 1% (e.g., 0.5-2%) of the total nut/seed/bean butter) is admixed/blended into the nut/seed/bean butter. The inoculated nut/seed/bean butter is then packaged, e.g., into jars, and allowed to fully crystallize. Approximately 48-72 hours more time is required for a nut/seed/bean butter to fully solidify (via crystallization of the hardening structuring fat that had been previously melted during grinding).

Predispersing the probiotic as a powder suspension in a free liquid oil to form a slurry and then blending the slurry into the substantially anhydrous fatty food helps assure the ultimate uniformity of dispersal of probiotic powder within the fatty food. The subsequent crystallization of structuring fat within an oil-rich food such as peanut butter assures long term uniformity of distribution of probiotic particles within the fatty food. Thus, the probiotic particles will lack any significant mobility that could cause the particles to settle out over time. Liquid oils suitable for use in making the probiotic particle slurry according to the present technology include any single liquid non-saturated vegetable oil or blend of vegetable oils described above, for example, salad oils, culinary nut/seed/bean oils, canola oil, corn oil, soybean oil, high oleic sunflower oil, safflower oil, and mixtures thereof. In the case of culinary nut/seed/bean butters such as peanut butter having a defined standard of identity, use of the nut/seed/bean oil corresponding to the nut/seed/bean butter is preferred, e.g., peanut oil for peanut butter. The liquid oil can be all of the same type, or mixtures of different oils may be used. In at least one embodiment, the liquid oil is a culinary nut/seed/bean oil selected from the group consisting of peanut oil, almond oil, hazelnut oil, cashew oil, pecan oil, pistachio oil, walnut oil, macadamia oil, Brazil nut oil, pumpkin seed oil, sesame seed oil, soybean oil, sunflower oil, safflower oil, chia seed oil, other culinary nut/seed/bean oils, and blends of two or more different nut/seed/bean oils. Saturated oils (e.g., palm oil, palm olein, palm kernel oil, coconut oil) are less preferred but could also be used.

The structuring fat is any fat that is capable of crystallizing at room temperature in the fatty food and thus stabilizes the fatty food, maintaining the fatty food in a solid state when stored at room temperature (20-25° C.). That is, use of the structuring fat protects against later oil separation after packaging. Without wishing to exclude other stabilizers, examples of suitable structuring fats and fat-related products include, for example, fully hydrogenated vegetable oils (e.g., hydrogenated canola oil, hydrogenated cottonseed oil, hydrogenated soybean oil), fatty acid mono- and diglycerides (such as glyceryl mono- and distearate and glyceryl mono- and dipalmitate), palm stearin obtained from the palm fruit or palm kernel, and mixtures thereof. In at least one embodiment, the structuring fat is present in an amount of 1% to 3% (e.g., 1%, 1.5%, 2%, 2.5%, or 3%) by weight of the substantially anhydrous fatty food.

The blending temperature is below a temperature that would kill or significantly diminish the proportion of viable bacteria in the probiotic bacterial preparation. In at least one embodiment, the blending temperature is within a range having a lower limit of about 100° F., about 105° F., about 110° F., about 115° F., about 120° F., about 125° F., about 130° F., about 135° F., about 140° F., or about 145° F., and an upper limit of about 105° F., about 110° F., about 115° F., about 120° F., about 125° F., about 130° F., about 135° F., about 140° F., about 145° F., or about 149° F., in any combination thereof. In at least one embodiment, the range is about 100° F. to about 120° F., about 100° F. to about 130° F., about 100° F. to about 140° F., about 110° F. to about 120° F., or about 110° F. to about 130° F. The blending temperature is preferably less than 150° F., which has been shown to kill many probiotic bacteria, and is preferably less than 140° F., less than 130° F., less than 120° F., or less than 110° F. Most structuring fats require many hours to substantially crystallize after having been diluted and melted (or melted and then diluted) into a fatty food. Thus, the blending temperature may be above the melting temperature of the structuring fat, or may be at or below the melting temperature as long as the structuring fat has not yet substantially crystallized.

In at least one embodiment, the fatty food is pasteurized or otherwise heated for a sufficient time and at a sufficient temperature to reduce or eliminate pathogenic bacteria such as *Salmonella* and/or *E. coli* species by at least 3 log (i.e., at least 99.9% kill rate), preferably 4-5 log (i.e., at least 99.99-99.999% kill rate), before cooling and adding the probiotic bacterial preparation. This includes heating at around 170±30° F. (typically 140-200° F.) for about 15 seconds to about 30 minutes. For products made from raw nuts, pathogenic bacterial levels are preferably reduced by 4-5 log (10,000-100,000-fold) by roasting at temperatures required to achieve the necessary reduction in bacterial levels. When vegetative probiotic species are to be added, pasteurization/roasting is preferably carried out before inoculation with the probiotic bacteria to avoid killing the probiotic bacteria. When only sporulated species are used, pasteurization/roasting can optionally be carried out after inoculation, as long as the probiotic species is more heat resistant than the pathogenic bacteria to be eliminated. Alternatively or in addition to pasteurization/roasting, processing may be carried out under aseptic conditions to prevent the introduction of pathogenic bacteria, particularly those such as *Salmonella* that have higher tolerance to heat.

Limiting the level of dissolved air/oxygen during food packaging may further stabilize probiotic bacteria and extend probiotic viability and shelf life. Liquid nitrogen and compressed nitrogen gas is substantially anhydrous and free of oxygen. Nitrogen is commercially used in manufacturing and packaging of many food products and may be useful for reducing the level of residual molecular oxygen in a food product containing probiotic species. To further aid in maintaining long term viability, anhydrous fatty foods such as culinary nut/seed/bean butters may also be packaged under nitrogen to be substantially free of molecular oxygen. Thus, in at least one embodiment, the substantially anhydrous fatty food is packaged under nitrogen.

These aspects of the present technology are further illustrated by the following examples.

EXAMPLES

The following examples are provided to illustrate embodiments of the present technology, but they are by no means intended to limit its scope. All of the references cited in the Examples below are hereby incorporated by reference in their entirety.

Example 1—Preparation of Probiotic Foods

A number of edible oils, fats, and fatty foods were supplemented with *Lactobacillus acidophilus* probiotic bacteria. Samples were prepared at room temperature (approximately 22° C.) and included peanut butter, substantially anhydrous butterfat (ghee), unsalted butter, Smart Balance margarine table spread (GFA Brands, Inc., Paramus, N.J.), palm olein, and soybean oil. Freeze-dried particles of *Lactobacillus acidophilus* (food grade 150 micron particles obtained from DuPont Nutrition and Health (New Century, Kans.)) were admixed and uniformly dispersed in these fatty foods and fats and oils. Vortex blending was used for mixing oils and low speed blade blending was used to mix probiotic powder into the solid fats and peanut butter. Probiotic powder was added at a level to provide approximately 1 billion viable bacteria per serving of food. In the case of peanut butter, the probiotic powder was first added to peanut oil to make a slurry and the slurry then blended into the peanut butter. In the case of the other samples, the probiotic powder was added directly without the use of a slurry.

Example 2—2-Month Survival Assay

The fatty foods described in Example 1 above were stored either under refrigeration (4° C.) or at room temperature (22° C.) for a period of two months during which samples were periodically assayed for their levels of viable CFUs. Results indicate a rapid decline in bacterial viability for butter and margarine but not for peanut butter, anhydrous butterfat, and palm olein. These findings may provide the basis for producing and selling probiotic peanut butter and other culinary nut/seed/bean butters, and possibly other substantially anhydrous fat-based foods such as butterfat (aka ghee). It is hypothesized that an environment of anhydrous fat stabilizes dormant viable probiotic bacteria that are dispersed in the fat. It is further hypothesized that an edible fatty food such as butter or margarine that contains latent moisture (e.g., in the form of a water-in-oil emulsion where moisture can migrate into otherwise dry and dormant probiotic particles) destabilizes the dormant probiotic bacteria, resulting in loss of viability.

Figure 1:
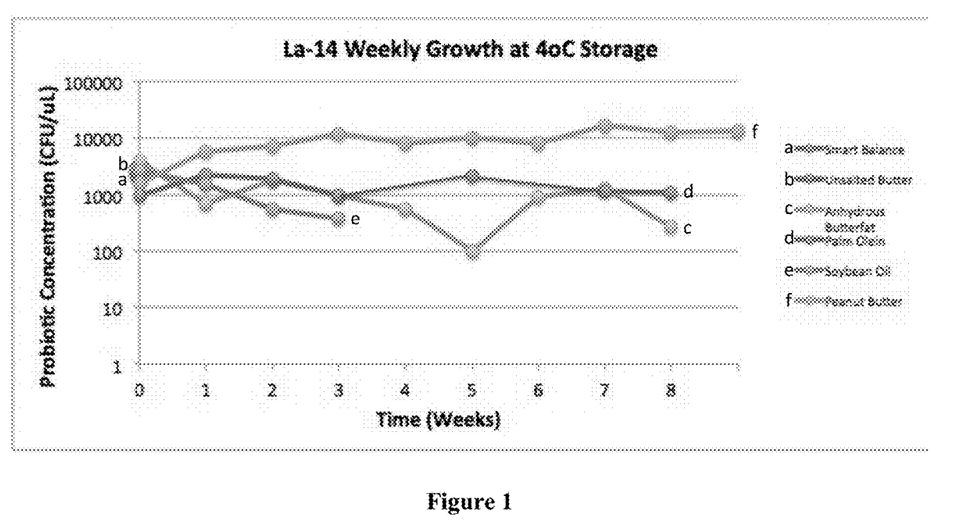
Figure 2:
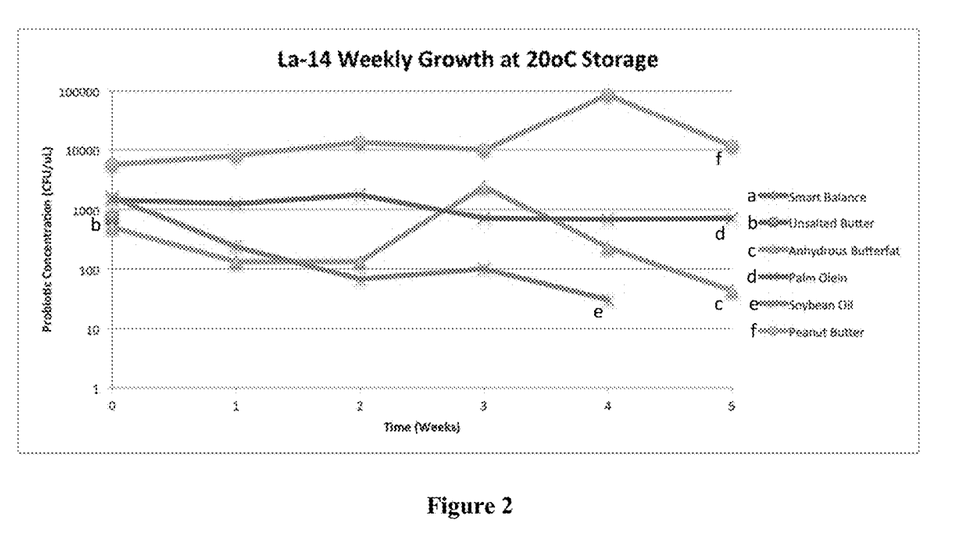

FIGS. 1 and 2 provide bacterial viability data (measured as CFU or "colony forming units") showing that the *Lactobacillus acidophilus* probiotic species is able to survive when stored in some of the oil-based environments including peanut butter, anhydrous butterfat and palm olein (and to a lesser extent in soybean oil) both under refrigeration (4° C.) and at ambient temperature (20° C.). However, conventional unsalted butter and Smart Balance margarine-type table spread, each containing approximately 20% water, did not provide a similar stabilizing environment, and no viable CFUs were recovered from these materials following initial plating (time zero). It is believed that substantially anhydrous edible fats and oils and substantially anhydrous oil-saturated foods such as peanut butter (and other culinary nut/seed/bean butters) can provide an environment compatible with long term survival and viability of probiotic microorganisms, provided that the microorganisms have been dried before their dispersal into the fat, oil or oil-saturated food.

Example 3—12-Month Survival Assay

A freeze-dried powder containing solely *Lactobacillus casei* bacteria (Lc-11 product obtained from DuPont Nutrition and Health, New Century, Kans.) was dispersed first as a concentrated powder suspension in peanut oil. This suspension was then admixed into warm peanut butter (creamy style) before fluid (melted) structuring fat within the peanut butter had any time to solidify. Based upon product specifications provided by the manufacturer, five hundred million bacteria were added per 32 g serving of peanut butter. This inoculation resulted in a bacterial titer of 15,600,000 *L. casei* per gram of peanut butter. As shown in Table 1, a significant percentage survived after storage at room temperature for 12 months.

TABLE 1

| 12-Month Survival at Room Temperature[†] | |
|---|---|
| Months after Production | CFU/g Peanut Butter |
| 0 (time of production) | 15,600,000 |
| 5 | 16,000,000 |
| 7 | 20,000,000 |
| 10 | 43,000,000[‡] |
| 11 | 18,000,000 |
| 12 | 12,000,000 |

[†]The commercial-scale samples used in this study were prepared by Golden Boy Foods (Fitzgerald, GA). Microbial testing was performed by JLA International (Albany, GA).
[‡]It is believed that the sample size plated at 10 months in Petri dishes on MRS agar was twice as large as intended and produced a CFU count of 43 million rather than 21.5 million.

Example 4—Use of Fully Stabilized Culinary Nut Butters for Sustained Viability of Vegetative Probiotic Microorganisms To produce useful commercially manufactured probiotic-supplemented culinary nut butters such as peanut butter, cashew butter, almond butter, hazelnut butter and the like prepared with vegetative probiotic microorganisms such as those of the bacterial genera Lactobacilli and Bifidobacteria, a substantial proportion of the originally added microorganisms must remain viable at least until the consumer utilizes the product. The survival of viable microorganisms is typically monitored by counting colony-forming units (CFU), i.e., bacterial colonies, cultured and counted in Petri dishes containing solid nutrient growth medium. To be useful, at least 10%, but preferably 25%, 50%, or even 75% or more of the probiotic microorganisms originally combined into the nut butter must survive the manufacturing and subsequent packaging, shipping and storage period up to the time the consumer consumes the product. As described and utilized in the present invention, a variety of probiotic microorganism species are commercially available and are particularly useful when prepared and utilized as dried particulate powders. These particles are often prepared by freeze-drying moist cultured bacterial cells and subsequently milling the dried material to produce sized particles typically in the 25 micron to 150 micron diameter size range.

It has been generally reported that so-called "natural style" peanut butter (semi-fluid at room temperature with peanut oil separating from peanut solids), is poor in sustaining the viability of probiotic bacteria at room temperature over a period of several months. Klu et al., "Survival of Four Commercial Probiotic Mixtures in Full Fat and Reduced Fat Peanut Butter," *Food Microbiol.* 44:34-40 (2014), found that when probiotic bacterial powders were admixed for 15 minutes at room temperature into solid hydrogenated vegetable oil-stabilized peanut butters using beater blending agitation, probiotic bacteria suffered similar substantial losses of viability (i.e., 1 to 3 log decreases at room temperature over a period of 12 months storage). Such beater blending disrupts the solid fat structure in a stabilized peanut butter, resulting in free peanut oil release and yielding a semi-fluid product. Interestingly, when Klu et al. stored the same beater-blended peanut butters at 4° C., probiotic bacterial viability was much greater over the same 12 month period. However, cold storage is inconvenient and, at 4° C., a beater-blended stabilized peanut butter becomes too solid for convenient manipulation or spreading. Thus, compositions like those described in Klu et al., with their poor probiotic viability at room temperature, are likely to have only limited commercial utility and such peanut butters have not appeared in commerce in the U.S.

As described in Example 3 above, it has been discovered, surprisingly, that a properly and fully stabilized peanut butter (solid at room temperature with no free peanut oil) that had been previously inoculated with freeze-dried vegetative probiotic bacteria before the structuring fat had solidified was able to sustain and deliver a substantially constant number of probiotic bacteria per gram of peanut butter, even when stored at room temperature over a 12-month period. Without wishing to be bound by theory, it is theorized that the Klu et al. peanut butters showed a limited ability to sustain high viability at room temperature and/or deliver a constant number of probiotic bacteria per gram due to one or more of the following problems: When a nut butter is not fully stabilized (i.e., not fully solidified by a structuring fat) and a significant portion of the oil (such as 10% or more) remains fluid, then a portion of the dispersed probiotic particles may settle downward through the nut butter under the force of gravity causing probiotic-depleted portions of the product. Additionally, if a culinary nut butter such as peanut butter is not fully solidified by a structuring fat, the mobility of the peanut oil in the butter (i.e., oil movement via convection and diffusion) is expected to promote loss of probiotic viability via oxidation and peroxidation. More specifically, airborne oxygen readily dissolves in peanut oil at a concentration of approximately 200 mg/kg at 25° C., 1 atm. Furthermore, free radical peroxides tend to form via oxidation of the polyunsaturated fatty acid, linoleic acid, that is abundant in nut oils such as peanut oil (32% linoleate). Together, these pro-oxidants are expected to substantially diminish the number of viable probiotic bacteria when the pro-oxidants are present in any non-stabilized oil (mobile/unsolidified oil) found in a culinary nut butter.

In previous probiotic-supplemented culinary nut butters, powders containing either single species or blends of multiple species of probiotic bacteria have been utilized to produce a number of supplemented peanut butters. (E.g., Klu et al. "Survival of *Lactobacillus rhamnosus* GG as Influenced by Storage Conditions and Product Matrixes," *J. Food Sci.* 77(12):659-63 (2012); Klu et al., "Survival of Four Commercial Probiotic Mixtures in Full Fat and Reduced Fat Peanut Butter," *Food Microbiol.* 44:34-40 (2014), each of which is hereby incorporated by reference in its entirety.) The survival of probiotic bacteria in these peanut butters stored at 4° C., 25° C., and 37° C. over a 12-month period has been reported in these published references. Klu et al. report that while at 4° C. most probiotic species maintained their viability over the 12-month period in both full fat and reduced fat peanut butters, the viability of these same bacterial populations at 25° C. (measured as CFU per gram peanut butter) decreased approximately one to three logs while at 37° C. viabilities decreased 2.5 to 3.8 logs for some species, while other species decreased to undetectable levels. It was theorized that the inoculation method used by Klu et al. for combining probiotic culture powders into the commercial peanut butters used by Klu et al. (produced by the American Blanching Company in Fitzgerald, Ga.) caused damage and compromised certain properties of the original commercial peanut butter. More specifically, the dispersal method described in the Klu et al. publications includes warming the commercial peanut butters to 37° C. for 6 hours and then adding each probiotic powder mixture and vigorously mixing and beating the peanut butter at room temperature for 15 minutes. This treatment will disrupt the delicate crystalline fat structure that exists in commercial stabilized peanut butter. This fat crystallization occurs over a 2-3 day period after jars are filled with hot peanut butter containing a solid structuring fat (e.g., hydrogenated vegetable oil such as hydrogenated canola, cottonseed and/or soybean). Protecting the crystalline structure of the structuring fat within the peanut butter prevents peanut oil separation that otherwise occurs over a few days when natural peanut butter is stored at room temperature. The 37° C. warming temperature used by Klu et al. is insufficient to cause any significant re-melting of the hydrogenated structuring fat. Therefore, after the detailed vigorous blending of their peanut butter, liquid peanut oil is released within the peanut butter and this oil constituting approximately 50% by weight of the total peanut butter, inevitably contacts and surrounds the probiotic powder particles.

To evaluate this theory, a number of different commercial particulate preparations of probiotic bacteria were obtained, including the following three freeze-dried species with the following titers of viable bacteria per gram of powder: *Lactobacillus acidophilus* (La-14, $2 \times 10^{11}$ CFU/g), *Lactobacillus casei* (Lc-11, $3 \times 10^{11}$ CFU/g), and *Bifidobacterium lactis* (Bl-04, $5 \times 10^{11}$ CFU/g) (all sold by DuPont Nutrition and Health, New Century, Kans.). Microscopic examination on a 50 micron calibration grid (150× magnification) showed that these powders are angular and fractured in appearance (likely from milling), with the bulk of the powders having diameters ranging between approximately 50 μm and 100 μm. Each of these powders was suspended at a concentration of 25 mg/ml in peanut oil (density 0.91 g/cm$^3$) and layered on top of 2 g samples of glycerine (density 1.26) and carbon tetrachloride (density 1.58) in glass test tubes at room temperature. The test tubes were then briefly centrifuged. Within 10 minutes approximately 50%, and within 30 minutes approximately 90%, of the powders had settled through the oil to the bottom of the tubes. These results show that these bacterial powders have considerably greater densities than that of the peanut oil (i.e., exceeding 1.58). Thus, if added to a peanut butter containing free oil (e.g., a natural peanut butter or a stabilized peanut butter whose crystalline fat structure has been disrupted by blending/heating) the bacterial powders over time will tend to settle downward through the peanut butter. However, if a structuring fat such as hydrogenated vegetable oil or natural palm stearin (all solid at room temperature and at 37° C.) is melted at a higher temperature (e.g., 60° C.) in a hot peanut butter and then cooled and allowed to crystallize without physical disruption, the structuring fat will hold probiotic bacterial powders in homogeneous suspension indefinitely. By contrast, it is believed that the Klu et al. process, that included vigorous blending of probiotic powders into previously stabilized commercial peanut butters, caused release of free peanut oil. This treatment, producing a more fluid peanut butter, may have caused a loss of homogeneity with gradual settling out of probiotic microorganisms. The sampling of such peanut butters over a period of months by Klu et al. showed decreases in CFU/g for peanut butters both at room temperature and at 37° C. Again, these decreases may have been caused either by settling out of bacteria or because a more fluid peanut butter might allow more exposure and poorer protection against physical and chemical environmental insults, resulting in a more rapid loss of bacterial viability. On the other hand, the sampling of peanut butters stored at 4° C. over 12 months by Klu et al. showed very little loss in viability measured by CFU/g peanut butter. This further supports the above hypothesis, because peanut butters that contain free peanut oil and are partially fluid at room temperature become solid at 4° C. This liquid-to-solid phase change may explain why Klu et al. observed superior viability at 4° C. compared to the higher temperatures over the 12-month storage interval.

As described herein a method for more easily achieving homogeneous and long-term dispersal of a probiotic bacterial powder in peanut butter has been developed by utilizing freshly milled peanut butter that when initially milled is at a temperature of approximately 74° C. Various ingredients are added to the peanut butter including sugar and/or molasses as sweetener, salt to enhance flavor, and structuring fat such as hydrogenated vegetable oils or palm stearin to prevent later peanut oil separation after packaging the peanut butter in jars. The peanut butter with added ingredients is actively cooled in a scrape-surface heat exchanger. As the peanut butter cools to between approximately 37° C. and 41° C. but not more than 46° C., probiotic bacteria are added. Following this addition, generally 48 to 72 hours is required to achieve full crystallization and hardening of the peanut butter in the jar. This full crystallization assures that probiotic bacterial particles will remain homogeneously distributed throughout a jar of peanut butter for the life of the peanut butter, e.g., for a year or more. Viability tests over 12 months for peanut butter stored at 20° C. and containing *Lactobacillus casei* show there is no measurable decrease in the number of viable probiotic bacteria per gram of peanut butter containing between approximately $2\times10^7$ and $8\times10^7$ CFU/g peanut butter manufactured and stabilized according to the protocol described below.

The method described herein differs from that of Klu et al., in which a probiotic powder mixture is added directly into a previously stabilized crystalline peanut butter that has been subjected to orbital and beater mixing for 15 minutes at room temperature. It has been pointed out that this vigorous agitation disrupts the crystalline network of structuring fat and substantially re-liquifies the peanut butter. By comparison, the present method has shown that more convenient and homogeneous dispersal of probiotic bacterial powders is achieved with greater convenience, greater time-savings and lower cost if a probiotic powder is first suspended in peanut oil with its relatively low viscosity compared to peanut butter. For example, one gram of a probiotic powder such as *Lactobacillus acidophilus* La-14 powder containing $2\times10^{11}$ CFU/g can be readily diluted and dispersed in 49 g of peanut oil to provide a bacterial suspension of $4\times10^9$ CFU/g oil. Then, by diluting this bacterial suspension 100-fold further into peanut butter, a bacterial titer of $4\times10^7$ CFU/g peanut butter is obtained. For a 32 g serving of peanut butter, the serving will provide approximately 1.3 billion CFU of probiotic bacteria. Because the above method employs solid bacterial particles suspended in peanut oil (homologous to peanut butter itself being a suspension of peanut solids in peanut oil), this peanut oil dispersal method for bacterial particle dispersal in peanut butter is achieved with a minimum of mixing. Also, because the U.S. FDA Standard of Identity for peanut butter allows addition or substraction of peanut oil as long as the fat content of the finished peanut butter does not exceed 55%, the addition of probiotic particles via approximately 1% added peanut oil is non-controversial.

In the method described herein, bacterial particle dispersal is performed before the peanut butter undergoes structuring fat crystallization to prevent any eventual settling out of bacterial particles. This crystallization occurs after the peanut butter is packed in jars at the end of its manufacture. This differs from the method of Klu et al. in which dispersal of probiotic bacterial powder involves mechanical blending and beater-disruption of the structuring crystalline fat structure. As explained above, this blending process liberates free peanut oil that may limit the ability to sustain high bacterial viabilities and/or degrade the homogeneity of dispersed probiotic bacterial powders in such peanut butters stored at room temperature. Furthermore, probiotic powders appear to be susceptible to clumping and non-uniform dispersal when blended directly into viscous peanut butter (method of Klu et al.) compared to the present method of initial suspension and dispersal in peanut oil, with subsequent dilution and dispersal of this oil suspension into peanut butter.

Example 5—Sporulated, Heat-Resistant Bacteria

If a food product requires processing at elevated temperature (e.g., for pasteurization), it may be desirable to incorporate a probiotic bacterial species having increased resistance to heat. For example, a spore-forming probiotic species such as *Bacillus coagulans* may be required if the probiotic species is to be added to a food product before heat-processing (e.g., a food requiring subsequent processing at 150-180° F.). Thus, freeze-dried spores of *B. coagulans* (e.g., obtained from Ganeden Biotech Inc. Cleveland, Ohio or Nebraska Cultures, Walnut Creek, Calif.) may be preferred over freeze-dried vegetative bacterial species for assuring probiotic survival in a heat-processed canned food product. However, *B. coagulans* spore supplementation is typically five to ten times more costly than vegetative Lactobacilli cell supplementation (approximately 0.8 cents vs. 0.15 cents per serving) at comparable levels of supplementation, e.g., $10^9$ CFU per serving. Furthermore, the biofunctional diversity of numerous and less costly vegetative bacterial species is advantageous when compared to the single probiotic spore-forming species (*B. coagulans*) that is commercially available. Therefore where the temperature level and/or dwell time at elevated temperature can be limited, e.g., adding probiotic bacterial powders late in the food processing cycle, it is possible to maintain full probiotic viability for vegetative probiotic bacterial species in the finished food product. This has proven possible in the heat processing and packaging of culinary nut butters such as peanut butter where probiotic bacterial powders can be added to the nut butter as the product is cooling.

Example 6—Microparticulate Probiotic Bacterial Preparations

Preferably, the probiotic bacteria are provided in the form of solid microparticles that are themselves substantially anhydrous. Probiotics in the form of anhydrous microparticles are commercially available and have been found to be easy to disperse in fats and oils. There is no detectable grittiness in the texture of fats containing these microparticles upon mastication. Furthermore, there was no disagreeable flavor imparted to the fat or oil when suitable titers of probiotic bacteria (e.g., $10^9$ CFU per 15 ml serving of oil or fat) were admixed into fats and oils. Furthermore, with the fat-based vehicle selected herein being paste-like and/or spreadable such as a culinary nut/seed/bean butter and solid or semi-solid anhydrous butterfat with an elevated viscosity (i.e., >50,000 centipoise at storage and usage temperatures), there is little to no tendency for homogenously dispersed probiotic bacterial particles to separate or become segregated from the food vehicle, even if there is a density difference between the bacterial particles and the surrounding food medium.

Microencapsulation produces cohered dried masses of bacteria (aka conglomerated bacteria) in the form of particles having an average diameter ranging from approximately 10 to 250 microns. Based on these particle sizes, the particles each contain many tens of thousands or more of bacteria. The substantial size of these particles is important for several reasons. If the powder particles are smaller, mechanical handling and airborne bacterial dust can become a problem. Fine powders can also be more difficult to wet and suspend in fluids such as peanut oil. Also, for maintaining long-term viability of probiotic bacteria, it is useful to minimize physical and chemical damage to individual bacteria. This includes loss of bacterial viability due to contact with dissolved oxygen in peanut butter and exposure to peroxide free radicals; larger particles are more resistant to these environmental insults than smaller particles.

There is little or no problem in keeping single bacterial cells or small groups of cohered cells (e.g., tens or hundreds of bacterial cells) suspended in fluid and semi-fluid food products such as yoghurt, fruit juices, blended fruit or vegetable "smoothie" beverages, or even semi-fluid "natural style" culinary nut/seed/bean butters for example. Dried conglomerated cells rapidly disaggregate into single or small groups of cells and remain suspended in such aqueous media. In contrast, however, as demonstrated herein, dried conglomerated probiotic bacteria (e.g., freeze-dried particles) that have been saturated with peanut oil and placed in a test tube filled with peanut oil do not disaggregate into single bacterial cells. Rather, the particles settle downward as intact conglomerates because the oil-saturated particles have a buoyant density that is substantially greater than the oil and peanut solids in peanut butter. It has been found that settling can be prevented by solidifying probiotic peanut butter after adding the probiotic particles in order to keep the particles suspended and uniformly dispersed throughout the peanut butter. This solidification is generally achieved with the addition of a structuring fat such as hydrogenated vegetable oil or palm stearin that must be substantially melted in the peanut butter before adding the probiotic particles. As pointed out previously, the method of making probiotic peanut butter described by Klu et al. involved adding probiotic powders and vigorous blending to achieve dispersal of probiotic bacteria after the commercial peanut butter had been previously solidified. That blending would have permanently disrupted the solid structure (crystalline fat) in the peanut butter and allowed subsequent settling out of their probiotic bacterial powders.

Example 7—Water Activity

Water activity ($a_w$) in a food product is defined as the partial vapor pressure of water in the food divided by the partial vapor pressure of pure water at the same temperature.

A probiotic peanut butter has been previously described in U.S. Patent Application Publication No. 2007/0207133 to Wassell, in which probiotic microorganisms were dispersed in a hydrophobic component, e.g., in a continuous oil phase, such as peanut butter. That hydrophobic component was subsequently combined with an aqueous dispersion. In view of the findings described in Example 2 above (comparing bacterial viability in butter and margarine compared to peanut butter), it is believed that the presence of moisture in the Wassell formulation compromised probiotic viability. By contrast, described herein is the use of a substantially anhydrous fatty food (e.g., culinary nut/seed/bean butter such as peanut butter or almond or cashew butter) that contains a very low level of water activity ($a_w$) ranging from about 0.2 to 0.8 or from about 0.3 to 0.7. Such low but measurable water activities enable killing of most pathogenic bacteria when combined with an adequately elevated temperature and exposure time interval. Accordingly, a culinary nut/seed/bean butter containing a low but adequate level of water activity is exposed to an adequately elevated temperature, e.g., approximately 160 F±20 F, for a sufficient period of time (e.g., 5-20 minutes). These conditions allow a manufacturer of nut butter to reduce or eliminate pathogenic bacteria, e.g., *Salmonella*. Reduction is defined as requiring at least a 3-log reduction of viable pathogen colony forming units (CFUs), i.e., at least a 99.9% kill rate, and preferably a 4- to 6-log reduction as measured by colonies counted on agar Petri dish solid nutrient media surfaces.

One approach to producing a pathogen-free probiotic-supplemented culinary nut/seed/bean butter is to add a probiotic bacterial species that is more heat-resistant than the pathogens being killed, e.g., adding the spore-forming probiotic strain, *Bacillus coagulans*. When exposed to the same elevated temperature, time interval and low level of water activity, *B. coagulans* spores are expected to maintain viability such that 50%-99% of the initially inoculated probiotic bacteria survive while the pathogen is killed. Alternatively and preferably, if the above-described heat level and dwell time is used to reduce or eliminate pathogens in a culinary nut/seed/bean butter, the temperature of the nut/seed/bean butter is subsequently reduced to a level of approximately 120° F. or less to allow full viability of admixed vegetative probiotic bacterial species (in the form of dried particulate powders as described above).

Culinary nut/seed/bean butters exemplified by peanut butters have been supplemented with approximately $10^9$ CFU per serving each of *Lactobacillus acidophilus* and *Bacillus lactis* dried powders, and have been stored at room temperature for approximately 1 year with little to no reduction in CFU levels.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A substantially anhydrous culinary butter selected from the group consisting of culinary nut butters, culinary seed butters, and culinary bean butters, wherein:
   (i) the substantially anhydrous culinary butter is solid at room temperature;
   (ii) the substantially anhydrous culinary butter comprises a structuring fat and a substantially anhydrous probiotic bacterial preparation; and
   (iii) the substantially anhydrous probiotic bacterial preparation is uniformly distributed within a crystalline matrix of the structuring fat and has a 12-month survival rate in the culinary butter at room temperature of greater than 10%.

2. The culinary butter according to claim 1, wherein the culinary butter has a water activity ($a_w$) at room temperature of less than about 0.8.

3. The culinary butter according to claim 1, wherein the culinary butter is selected from the group consisting of peanut butter, almond butter, hazelnut butter, cashew butter, pecan butter, pistachio butter, walnut butter, macadamia butter, Brazil nut butter, pumpkin seed butter, sesame seed butter, soybean butter, sunflower seed butter, safflower seed butter, chia seed butter, and combinations thereof.

4. The culinary butter according to claim 3, wherein the culinary butter is peanut butter.

5. The culinary butter according to claim 1, wherein the structuring fat is selected from the group consisting of fully hydrogenated vegetable oil, natural predominantly saturated fat, and mixtures thereof.

6. The culinary butter according to claim 1, wherein the depth of penetration into the culinary butter of a steel cone having a 60 degree conical angle and weighing 79g released from a zero drop height at room temperature is 5-20mm.

7. The culinary butter according to claim 1, wherein the culinary butter has a viscosity greater than 50,000 centipoise at room temperature.

8. The culinary butter according to claim 1, wherein the probiotic bacterial preparation has a water activity ($_w$) at room temperature of less than about 0.8.

9. The culinary butter according to claim 1, wherein the probiotic bacterial preparation is a vegetative probiotic bacterial preparation.

10. The culinary butter according to claim 9, wherein the probiotic bacterial preparation is a freeze-dried powder of one or more vegetative probiotic species.

11. The culinary butter according to claim 9, wherein the vegetative probiotic bacterial preparation further comprises a substantially anhydrous sporulated probiotic bacterial preparation dispersed therein.

12. The culinary butter according to claim 1, wherein the probiotic bacterial preparation comprises sporulated bacteria.

13. The culinary butter according to claim 1, wherein the probiotic bacterial preparation comprises bacteria selected from the group consisting of *Bacillus, Bifidobacterium, Lactobacillus, Lactococcus, Streptococcus, Pediococcus, Enterococcus, Leuconostoc, Carnobacterium, Proprioni bacterium*, and combinations thereof.

14. The culinary butter according to claim 13, wherein the probiotic bacterial preparation comprises bacteria selected from the group consisting of *Bacillus coagulans, Bifidobacterium adolescentis, Bifidobacterium animalis, Bifidobacterium bifidum, Bifidobacterium breve, Bifidobacterium essencis, Bifidobacterium faecium, Bifidobacterium infantis, Bifidobacterium lactis, Bifidobacterium longum, Bifidobacterium longum* subsp. *infantis, Bifidobacterium pseudolungum, Lactobacillus acidophilus, Lactobacillus boulardii, Lactobacillus breve, Lactobacillus bulgaricus, Lactobacillus casei, Lactobacillus delbrueckii* ssp. *Bulgaricus, Lactobacillus fermentum, Lactobacillus gasseri, Lactobacillus helveticus, Lactobacillus paracasei, Lactobacillus plantarum, Lactobacillus reuteri, Lactobacillus rhamnosus, Lactobacillus rhamnosus* GG, *Lactobacillus salivarius, Lactococcus lactis, Streptococcus thermophilus, Pediococcus acidilactici, Enterococcus faecium, Leuconostoc, Carnobacterium, Proprioni bacterium*, and combinations thereof.

15. The culinary butter according to claim 1, wherein the probiotic bacterial preparation is microencapsulated.

16. The culinary butter according to claim 15, wherein the probiotic bacterial preparation consists essentially of particles having an average diameter of about 10 to about 250 microns.

17. The culinary butter according to claim 1, wherein the probiotic bacterial preparation is present in a concentration of at least 5 million CFU/g after storage at room temperature for 12 months.

18. A method of making a substantially anhydrous culinary butter that comprises a substantially anhydrous probiotic bacterial preparation dispersed therein, said method comprising:
  (i) providing a slurry comprising a liquid oil and a substantially anhydrous probiotic bacterial preparation dispersed in the slurry;
  (ii) providing a substantially anhydrous culinary butter selected from the group consisting of culinary nut butters, culinary seed butters, and culinary bean butters, wherein the substantially anhydrous culinary butter is solid at room temperature and comprises a structuring fat; and
  (iii) blending the slurry into the substantially anhydrous culinary butter at a blending temperature, wherein the blending temperature is within the viability temperature range of the probiotic bacterial preparation and the structuring fat is substantially melted during said blending, wherein the substantially anhydrous probiotic bacterial preparation is uniformly distributed within a crystalline matrix of the structuring fat in the blended culinary butter and has a 12-month survival rate at room temperature of greater than 10% in the blended culinary butter.

19. The culinary butter according to claim 1, wherein the structuring fat is present in an amount of 1% to 3% by weight of the culinary butter.

20. The culinary butter according to claim 1, wherein the 12-month survival rate in the culinary butter at room temperature is greater than 25%.

21. The culinary butter according to claim 1, wherein the 12-month survival rate in the culinary butter at room temperature is greater than 50%.

22. The culinary butter according to claim 1, wherein the 12-month survival rate in the culinary butter at room temperature is greater than 75%.

* * * * *